US012652449B2

(12) United States Patent
Bourbon et al.

(10) Patent No.: US 12,652,449 B2
(45) Date of Patent: Jun. 9, 2026

(54) VISUALIZATION SYSTEM AND METHOD FOR TEMPERATURE STABILIZING A CURRENT OPTICAL SYSTEM STATE OF A VISUALIZATION SYSTEM

(71) Applicant: Scholly Fiberoptic GmbH, Denzlingen (DE)

(72) Inventors: Johannes Bourbon, Freiburg (DE); Cyril Autourde, Kunheim (FR)

(73) Assignee: Schölly Fiberoptic GmbH, Denzlingen (DE)

( * ) Notice: Subject to any disclaimer, the term of this patent is extended or adjusted under 35 U.S.C. 154(b) by 0 days.

(21) Appl. No.: 18/999,015

(22) Filed: Dec. 23, 2024

(65) Prior Publication Data

US 2025/0220286 A1 Jul. 3, 2025

(30) Foreign Application Priority Data

Dec. 28, 2023 (DE) .......................... 102023136773.0

(51) Int. Cl.
| | |
|---|---|
| *H04N 23/69* | (2023.01) |
| *H04N 23/51* | (2023.01) |
| *H04N 23/52* | (2023.01) |
| *H04N 23/67* | (2023.01) |
| *H04N 23/68* | (2023.01) |
| *A61B 34/30* | (2016.01) |
| *A61B 90/00* | (2016.01) |

(52) U.S. Cl.
CPC ............. *H04N 23/52* (2023.01); *H04N 23/51* (2023.01); *H04N 23/67* (2023.01); *H04N 23/687* (2023.01); *H04N 23/69* (2023.01);

*A61B 34/30* (2016.02); *A61B 90/37* (2016.02); *A61B 2090/371* (2016.02)

(58) Field of Classification Search
CPC ......... H04N 23/69; H04N 23/51; H04N 23/67
USPC ...... 348/208.99, 61, 207.99, 208.12, 208.11, 348/211.9
See application file for complete search history.

(56) References Cited

U.S. PATENT DOCUMENTS

| | | | |
|---|---|---|---|
| 2005/0099523 A1 | 5/2005 | Konishi et al. | |
| 2013/0048855 A1* | 2/2013 | Abreo ..................... | H04N 23/23 |
| | | | 250/330 |
| 2019/0107700 A1* | 4/2019 | Lee ........................ | A61B 90/20 |

FOREIGN PATENT DOCUMENTS

| | | |
|---|---|---|
| CN | 103124326 A | 5/2013 |
| CN | 104853126 A | 8/2015 |
| CN | 116908993 A | 10/2023 |
| JP | H07107369 A | 4/1995 |

(Continued)

*Primary Examiner* — Daquan Zhao
(74) *Attorney, Agent, or Firm* — Volpe Koenig

(57) ABSTRACT

For improved operation of a visualization system, which includes an imaging optical unit having an adjustable zoom optical unit and a likewise adjustable focusing optical unit, it is provided that with the aid of at least one temperature detector, at least one detection temperature is registered inside the imaging optical unit, either directly sensorially and/or indirectly (for example via an estimation) and that with the aid of a stabilization system, which includes one or more stabilization control loops, the focusing optical unit and/or the zoom optical unit is actively adjusted as soon as a temperature threshold value is exceeded with respect to a currently registered temperature change of this detection temperature.

20 Claims, 3 Drawing Sheets

(56)     References Cited

FOREIGN PATENT DOCUMENTS

| JP | 2003255423 | A | 9/2003 |
| JP | 2019022175 | A | 2/2019 |

* cited by examiner

VISUALIZATION SYSTEM AND METHOD FOR TEMPERATURE STABILIZING A CURRENT OPTICAL SYSTEM STATE OF A VISUALIZATION SYSTEM

CROSS-REFERENCE TO RELATED APPLICATIONS

This application claims priority from German Patent Application No. 10 2023 136 773.0, filed Dec. 28, 2023, which is incorporated herein by reference as if fully set forth.

TECHNICAL FIELD

The invention relates to a method for temperature stabilization of a current optical system state of an, in particular medical, visualization system. This system comprises an imaging optical unit having an adjustable zoom optical unit for defining a current zoom level and an adjustable focusing optical unit for defining a current spatial location of a focal plane, and having at least one image sensor. In the method, at least one image of an object observed using the visualization system, for example an operation area, is recorded with the aid of the at least one image sensor. Furthermore, the current optical system state, which comprises the current optical zoom level and the current spatial location of the focal plane, is stabilized in relation to temperature-related variations within the imaging optical unit with the aid of the method.

The invention additionally relates to a visualization system, which can preferably be designed as part of a robotics system and/or as a medical visualization system. This visualization system has an imaging optical unit, which comprises the following components: an adjustable zoom optical unit for defining a current optical zoom level; an adjustable focusing optical unit for defining a current spatial location of a focal plane; and at least one image sensor for recording at least one image of an object observed using the visualization system, for example an operation area; and finally at least one temperature detector, which is configured for the direct sensorial measurement and/or indirect non-sensorial registration of at least one current temperature change of a detection temperature within at least one detection area.

BACKGROUND

Medical visualization systems in the form of exoscopes are already previously known in the prior art, which are used as part of a robotics system in neurosurgery in order to visualize an operation area for the neurosurgeon in an enlarged representation on a display screen. In such an application, the exoscope is arranged by a robot arm at different working distances (typically 200-550 mm) from an operation area to be observed, wherein the visualization system is embodied via a zoom optical unit for changing an optical zoom level (and therefore the respective image detail recorded with the aid of the image sensor) and a focusing optical unit for spatially defining a focal plane.

In such a visualization system, in addition to stepping motors for adjusting the zoom and focusing optical units, numerous other electronic structural units are typically also installed, for instance the image sensor, regulation and readout electronics, and an electronic image processing unit. All of these electronic components display an electrical power loss, which results in heating of the overall system, in particular the imaging optical unit.

In operation of the visualization system, individual components initially heat up in a type of "warm-up" phase initially from approximately 25° C. room temperature to temperatures in the range of 40° C. to approximately 60° C., wherein still further heating can also occur during the actual operation. However, this warm-up typically takes place even before the surgeon begins to work with the visualization system at all. This initial heating is insofar comparatively noncritical.

During the use of the visualization system, however, temperature changes of 10° C. and more can occur for different reasons (varying electrical waste heat, changes of the temperature within the operating room, etc.), which in the worst case can result in a change of the focal plane of multiple centimetres (in the extreme case up to 80 mm has been observed).

The change of the temperature not only has an effect here on a change of the index of refraction of the respective lens material, but also changes the shape of the respective lens, its position, possibly its orientation/tilt, wherein it is also to be taken into consideration here that the mechanical structure in which the lenses are held is also subject to thermo-mechanical tensions which have an effect on the optical function. All of these effects generally have the result that the focal length of the focusing optical unit and the focal length of the zoom optical unit and therefore the resulting zoom level can change significantly because of temperature. Such a thermal drift of the imaging optical unit can be extremely annoying to the surgeon during use of the visualization system.

This is true in particular if the visualization system has multiple parallel optical channels, for instance for stereoscopic vision, and the spatial position of observed objects is to be determined on the basis of measured data of both channels (such a design can also be provided in a visualization system according to the invention). Such approaches permit, for example, measuring functions or objects within a live video image to be optically tracked. Furthermore, this is also of interest, for example, for the documentation of medical interventions or also permits the specific positioning of objects within the field of view observed with the aid of the robot system. However, all of these functions are impaired by the described thermal drift.

In a stereoscopic display, interfering effects can moreover also occur if the focal plane or the zoom level (and therefore the size of the field of view) of the two stereo paths changes by different amounts as a result of a temperature change. Such drifting-apart of the two optical channels of the visualization system can arise, for example, due to a nonhomogeneous temperature distribution within the camera head and/or because the two optical paths are located at different positions within the overall system, which are negatively affected to different degrees by a system component generating waste heat.

SUMMARY

Proceeding from this background, the invention is based on the object of effectively counteracting temperature effects, in particular thermal drifts, which have a negative effect on the performance of the visualization system.

A method with one or more of the features according to the invention are provided in order to achieve this object. In particular, it is therefore provided according to the invention to achieve the stated object in a method as described at the outset for the temperature stabilization of a current optical system state of a visualization system that with the aid of a stabilization system, which comprises at least one stabilization control loop, at least one current temperature change of a detection temperature within at least one detection area within the visualization system is registered progressively, directly or indirectly, and that the focusing optical unit and/or the zoom optical unit is actively adjusted by the at least one stabilization control loop as soon as at least one temperature threshold value for the at least one current temperature change is exceeded.

A direct registration of the change of the detection temperature can be achieved, for example, by means of a temperature sensor. However, the change can also be registered indirectly, for example with the aid of a sensor which registers a length change caused by the temperature change or another temperature-related mechanical change within the imaging optical unit.

In other words, the invention therefore proposes stabilizing the optical system state by means of a stabilization system having at least one stabilization control loop and by registering at least one temperature change of a detection temperature. In particular thermally related adjustments of the zoom and/or focusing optical unit can thus be compensated for by corresponding readjustment (active readjustment on the basis of the directly or indirectly registered temperature change). This makes it possible, in a specific operating point which a user of the visualization system has just selected (thus, for example, for a just set zoom level and/or a specific currently selected focal plane), to implement a temperature regulation which keeps this operating point stable, in particular independently of whether and how the temperature changes within the visualization system (in particular within a housing which houses the imaging optical unit).

Preferably, at least two detection temperatures can be evaluated in this method, which are registered in different detection areas within the visualization system, preferably within the imaging optical unit. Such a spatially distributed registration of the temperature is not absolutely necessary; however, it can be advantageous, for example, for the stabilization of the optical zoom and therefore can be reasonable. The registration of the current temperature change can take place here as already mentioned directly, for example with the aid of a temperature measurement, or else indirectly, for example in that a temperature-dependent position change is registered, from which a conclusion about the temperature change that has occurred is possible.

The visualization system can be embodied, for example, as a medical visualization system and/or, for example, as a stereoscope or microscope or exoscope. A further, more striking advantage of the method according to the invention results in this way, namely that the corresponding temperature stabilization, for example in the context of a stereoscopic intervention, prevents the stereoscopically recorded image of the operation area from being corrupted due to temperature variations and thus due to the zoom level possibly changing in this way and/or the thermally related change of the spatial location of the focusing optical unit. Due to the temperature stabilization of the current optical system state of the visualization system, a uniformly high quality of the recorded image or the recorded image series, for example a live video image, can thus be ensured. If the visualization system has a stereoscopic imaging system, respective optical system states of the respective optical channel can be prevented from drifting apart from one another by means of the invention.

The visualization system can thus be equipped, for example, with two parallel optical channels and two image sensors in each case, so that a stereoscopic imaging system is provided which conveys a three-dimensional impression to the surgeon. The visualization system can also register objects such as operation instruments within the live video image in this case. The visualization system can furthermore be configured to calculate a spatial position of the respective object in a world coordinate system on the basis of a model of the stereo optical unit and with application of triangulation. For this purpose, it can be provided that a location position within the camera coordinate system is initially assigned to each pixel of the image sensor within the respective camera coordinate system (in particular of a left or right image sensor). Subsequently, as a function of the or a set zoom level and the current position of the focal plane/setting of the focusing optical unit, a corresponding coordinate in the world coordinate system can be assigned to this location. This approach allows, for example, measurement functions or objects within the live video image to be optically tracked. Furthermore, this is also of interest, for example, for the documentation of medical interventions and/or this can also enable the specific positioning of objects within the field of view observed with the aid of a robot system.

The problem exists in principle that a continual adjustment of the optical unit, also due to mechanical tolerances, can cause image wobbling which can be very annoying. To avoid this continual adjustment, it is provided that a hysteresis be introduced: for this purpose, it can be provided that to avoid image wobbling of the at least one image recorded by the visualization system, the at least one stabilization control loop is designed having an artificial hysteresis. This artificial hysteresis can preferably be electronically implemented. In this way, the advantage of substantially improved operating properties results for a user of the visualization system (for example for a surgeon carrying out a medical intervention), because the image wobbling is avoided.

The regulation implemented by the stabilization control loop can thus be designed so that it only intervenes above a threshold value with respect to a change in absolute value of the current temperature change of the registered detection temperature. If a temperature change above this threshold is registered by the stabilization system, the optical system state can be actively readjusted, for example in that a respective stepping motor is actuated in order to adjust the zoom optical unit and/or the focusing optical unit accordingly. In contrast, if only a temperature change in absolute value below this threshold is registered, the regulation does not intervene in the current case.

For example, the hysteresis can be designed so that if a minor short-term temperature increase of, for example, 20° C. to 21° C. is registered, an adjustment of the focusing optical unit and/or the zoom optical unit is not yet performed. On the other hand, the stabilization system can intervene via the at least one stabilization control loop, for example, if the temperature increases from 20° C. to 22° C., so that then the focusing optical unit and/or the zoom optical unit is actively adjusted and cooling then possibly occurs back to 21° C. (in this example). The hysteresis can therefore be set or defined, for example, with respect to a respective lens position. This has the result that the visualization system can nonetheless in each case be in a different system state (with respect to a current focal length of the focusing optical unit and the current zoom level) at the same temperature. This is because depending on whether the temperature approaches 22° C. starting from 21° C. or starting from 20° C., as in the above example, a different final regulated optical system state can result. Instead of an artificial hysteresis, fixed, predefined temperature threshold values can also be set, wherein the stabilization system intervenes as soon as one of these temperature threshold values is reached (thus the registered temperature reaches this value). This can be implemented, for example, in such a way that an active readjustment takes place in each case upon reaching a specific temperature (for example: 20° C., 23° C., 26° C.).

However, the invention has recognized that the size of the hysteresis should be limited for two reasons:

On the one hand, if the surgeon sets a high zoom factor, the so-called depth of field (DOF) can only still be a few millimetres, thus, for example, +/−1.5 mm. In this case, the stabilization system thus already has to intervene as soon as a current position of the focal plane has changed because of temperature significantly in comparison to the current DOF, thus, for example, by 1.0 mm. This is because if the stabilization system were only to intervene from a change of the location of the focal plane of 2 mm, for example, the current live image which the surgeon sees would become fuzzy, for example, since the temperature stabilization has not intervened in a timely manner. This is absolutely to be avoided. It can also be provided that the hysteresis is automatically adapted by the stabilization system depending on the currently selected zoom and/or depending on the working distance or depending on the current location of the focal plane.

On the other hand, for example, there are however also situations in which a particularly large working distance to the observed object is selected and a particularly low zoom level is set, so that a particularly large field of view results. If the world coordinates of objects within the camera live image are now to be determined in such a situation using the described triangulation approach, this is particularly susceptible to error with respect to temperature-related variations of the focal length of the focusing optical unit and the optical zoom level. This is because an absolute accuracy with respect to the location resolution in the determination of the world coordinates of an object of ideally 50 μm, but at least 100-300 μm, is to be achieved in use. To achieve such an accuracy in the determination of the position of the object in space, it is thus necessary for the temperature stabilization to intervene early in order to keep temperature-related deviations as small as possible.

The artificial hysteresis is preferably electronically implemented. It can thus be ensured, for example, that a minimum adjustment travel is maintained in each case upon the adjustment of the respective focusing optical unit/zoom optical unit, which is favourable for achieving a high accuracy in the adjustment. Stepping motors are preferably used for this purpose, which have the advantage of a very high repetition accuracy with respect to the position to be approached.

In particular, the at least one stabilization control loop, which is designed having the artificial hysteresis, can automatically initiate different adjustments of the focusing optical unit and/or the zoom optical unit depending on the current optical system state and/or depending on the direction of the registered current temperature change.

A surgeon therefore does not have to readjust the optical system state independently. These different adjustments are preferably also automatically initiated independently of whether a new target value for an adjustment of the focusing optical unit and/or the zoom optical unit is currently being specified from outside the at least one stabilization control loop, for example by the surgeon, or not.

It can be provided that at least one detection temperature is directly registered sensorially with the aid of a temperature sensor. The temperature sensor or the temperature sensors can be designed here, for example, as thermocouples (for example by means of a thin wire on a film) or as a thermistor. In addition, for example, parasitic temperature sensors can also be read out, which are already present in any case in a microcontroller or the respective image sensor, for example. The values of multiple temperature sensors can also be averaged or combined according to a calculation rule in order to achieve a higher stability of the regulation. This can be advantageous so that an (excessively large) active readjustment is not already initiated upon an only locally limited temperature change, which would cause only a smaller temperature-related adjustment of the optical unit.

Alternatively or additionally, it can be provided that at least one detection temperature is indirectly registered. The indirect registration of a detection temperature can be carried out, for example, by calculation on the basis of a current electrical power loss of an electronic component of the visualization system. Additionally or alternatively, an electronic activity level of an electrical component can also be taken into consideration for the indirect registration of a detection temperature.

The respective detection temperature is furthermore preferably progressively registered as a respective current temperature by the stabilization system. Furthermore, the mentioned current temperature change (on the basis of the respective registered detection temperature) can be determined in relation to a stored reference temperature. This reference temperature can preferably be adapted/updated by the stabilization system as soon as this system, more precisely a stabilization control loop, makes a regulation/ control intervention. In particular, in this way the optical system state can thus be actively adapted to the new reference temperature, so that the optical system state also remains stable at this new reference temperature (thus no noticeable change of the focal plane or the zoom level results for the surgeon in spite of a temperature change within the imaging system).

It can also be provided in the method that a temperature-related change of a spatial position of at least one component (for example a movable lens) of the imaging optical unit is sensorially registered. For this purpose, the visualization system can comprise position sensors, using which such position changes can be sensorially registered. Such temperature-related movements within the optomechanical imaging system can thus likewise initiate the temperature regulation algorithm which stabilizes the optical system state. This is because a detection temperature can also be at least indirectly registered via such position changes.

In other words, it can thus be provided that the focusing optical unit and/or the zoom optical unit is actively adjusted by the at least one stabilization control loop as soon as at least one position threshold value for the at least one sensorially registered, temperature-related position change is exceeded. Temperature-related can be understood here to mean that the spatial position of the component inadvertently changes due to a temperature change, in particular beyond a defined threshold value.

In a further advantageous embodiment of the invention, it can be provided that the respective adjustment of the focusing optical unit and/or the zoom optical unit takes place at different times in relation to the registered at least one current temperature change depending on the current optical system state, in particular depending on a current adjustment of the focusing optical unit and the currently set zoom level.

Depending on which optical system state the imaging optical unit is currently located in, the stabilization system will already make a regulation intervention in the event of temperature changes of different amounts in order to stabilize the current optical system state. It is thus possible to prevent, for example, that in a first system state, frequent but actually unnecessary early adjustment of the optical unit takes place, while in a second system state, the adjustment simply does not take place early enough.

In particular, the at least one temperature threshold value can be adapted depending on the current optical system state, so that the temperature stabilization intervenes in a stabilizing manner upon smaller or only upon larger temperature changes of the detection temperature, depending on the current optical system state.

In one advantageous embodiment of the invention, it can be provided that the at least one stabilization control loop operates even if no new optical system state is specified by the visualization system itself or by a user as a target specification. In particular, an optical system state which has been set once is thus progressively stabilized in relation to temperature variations by the stabilization system (by means of an active autonomous regulation which the stabilization system implements).

The optical system state can thus be progressively stabilized by the stabilization system, specifically without the user noticing the controlling intervention of the stabilization system in a live image recorded using the at least one image sensor. A user of the visualization system, for example a surgeon, can therefore use the visualization system undisturbed.

In a further advantageous embodiment of the invention, it can be provided that if the at least one temperature threshold value and/or the at least one position threshold value is exceeded, the at least one stabilization control loop actuates at least one actuator of the focusing optical unit and/or the zoom optical unit. A correspondingly early active readjustment of the zoom and/or focusing optical unit can be generated in this way.

In particular, the actuator can be a stepping motor.

The at least one stabilization control loop can actuate the respective actuator in particular mediated via a separate respective control loop. The actuator can thus be adjusted in a regulated manner with the aid of this separate control loop.

In a preferred embodiment of the visualization system, it is provided that the stabilization system, for example via a respective stabilization control loop, actuates at least two actuators, in particular at least two stepping motors, of the zoom optical unit and at least one actuator of the focusing optical unit. For example, the stabilization system can make a control intervention in at least two separate control loops for adjusting the zoom optical unit and in at least one further control loop of the focusing optical unit in order to adjust the respective actuator which is regulated by the respective control loop so that the registered temperature change, which results in a change of the system state, can be compensated for. One of the control loops of the stabilization system can also make a control intervention simultaneously on two actuators of the zoom optical unit, for example if the zoom optical unit is embodied by means of two lens pairs movable toward one another or away from one another.

As mentioned, an, in particular respective, (partial) stabilization control loop can also actuate multiple actuators as part of the higher-order stabilization system, wherein these actuators can also be assigned to the same optical functionality: the zoom optical unit can thus comprise, for example, two optical lens groups displaceable in relation to one another. In such a case, both of these optical lens groups can be actuated by the respective assigned stabilization control loop to compensate for temperature effects.

In this case, different positioning distances A and B (for a current optical system state) can be stored for each of the two lens groups (i.e. for example: group zoom 1: A μm/K, group zoom 2: B μm/K). In addition, it can be advantageous if the respective actuators, as already mentioned above, can be addressed by different partial stabilization control loops, i.e. are actuatable by means of multiple different partial stabilization control loops of the higher-order stabilization control loop. Such a regulation architecture can be understood as a single large overall stabilization control loop in the meaning of the invention, the individual partial control loops of which can compensate for different temperature-related disturbances, in order to thus stabilize the optical system state as desired against temperature changes. Thus, for example, one of the stabilization control loops which is predominantly to stabilize the focusing optical unit can also be configured to additionally actuate the zoom optical unit. Vice versa, a stabilization control loop which is predominantly to stabilize the zoom optical unit can also be configured to additionally actuate the focusing optical unit.

In particular, the respective actuator can be actuated to adjust the focusing optical unit and/or the zoom optical unit along an optical z axis of the imaging optical unit. It can be provided in this case that the at least one stabilization control loop actuates the respective actuator, mediated via a separate respective control loop, with the aid of which the actuator can be adjusted in a regulated manner.

The stabilization control loop, in particular a respective partial control loop, can also be designed here so that multiple control loops act simultaneously on one actuator. For example, the visualization system can be designed as parfocal, so that the focus does not change with the zoom. In such a design, it can then be necessary that a partial control loop of the stabilization control loop which addresses the zoom also acts on the actuator for the focus, so that this control loop can cause a simultaneous adjustment of the focusing optical unit and the zoom optical unit. This can be necessary, for example, if the focus has changed due to tolerances or other artifacts although the system is actually designed as parfocal. The control loop responsible for the zoom can thus also act on a focus actuator, even though a second partial control loop responsible for the focus does not recognize any cause to change the focus, for instance because the detected temperature change in the focus part is still below a specific threshold value.

In an advantageous embodiment of the invention, it can be provided that the stabilization system adjusts the focusing optical unit and/or the zoom optical unit by control as soon as the at least one current temperature change of the detection temperature exceeds an assigned temperature threshold value still permissible for the current optical system state. This preferably takes place independently of a respective target value, previously set by the user or by the visualization system, for an adjustment of the focusing optical unit and/or for an adjustment of the zoom optical unit.

In this case, in particular no target-actual value at all can be produced with respect to a respective regulation variable of the focusing optical unit and/or the zoom optical unit, for example a last specified focal length or a last specified optical zoom level. As a result, the stabilization system can thus also intervene in a stabilizing manner with respect to the optical system state if currently no instruction for adjusting the focusing optical unit and/or for adjusting the zoom optical unit is newly output by the user or by the visualization system.

In one advantageous variant of the method, it can be provided that the stabilization system adjusts the focusing optical unit and/or the zoom optical unit by control on the basis of a respective temperature model. The stabilization system in particular can deviate here from a last specified (by the user or by the system itself) respective target value in order to stabilize the current optical system state in relation to the registered at least one current temperature change. The respective temperature model can in particular model here a required temperature-dependent adjustment (for example $\Delta FL(T, \Delta T, FL, ZL)$) of the focusing optical unit or the zoom optical unit (for example $\Delta ZL (T, \Delta T, FL, ZL)$), for example as a function of a current detection temperature T, a registered change $\Delta T$ of the detection temperature (wherein it can be taken into consideration whether the change $\Delta T$ is positive or negative), a current focal length FL and/or a current zoom level ZL. It is to be mentioned here that the dimension of the focal length FL defines the spatial location of the resulting focal plane (thus that plane which is imaged sharply on the image sensor) along the optical axis. In order that the surgeon receives a sharp image, the focal plane thus has to coincide with the observed region.

It is accordingly preferred if the temperature model in this case takes into consideration the current optical system state (FL, ZL), in particular a current focal length FL of the focusing optical unit and/or a current zoom level ZL of the zoom optical unit.

A further advantageous embodiment of the invention provides that the stabilization system, preferably on the basis of the above-described temperature model or another temperature model, calculates a suitable compensating adjustment, in particular a respective suitable adjustment distance $\Delta z$ along a or the above-described optical z axis, of the zoom optical unit and/or the focusing optical unit on the basis of the registered at least one current temperature change. Thus, for example, a suitable adjustment distance $\Delta z$ can be determined in each case for an arbitrary registered temperature change, over which the focusing optical unit and/or the zoom optical unit accordingly has to be actively readjusted.

From the calculated adjustment, the stabilization system can then generate a respective actuation signal, in particular by intervention in a respective control loop, to adjust the zoom optical unit and/or the focusing optical unit. In this way, the current optical system state can then be stabilized in a temperature-dependent manner.

In a further advantageous embodiment, it can be provided in the method that the stabilization system takes into consideration a registered value of the current detection temperature T and adapts the at least one temperature threshold value $\Delta T_{max}(T)$ from which the stabilization system intervenes by control (for example as a result of an adaptation of a reference temperature). This adaptation preferably takes place after the stabilization system has intervened by control. This temperature-dependent adaptation of a temperature threshold value and/or the reference temperature enables, inter alia, the stabilization system, depending on the current location of the detection temperature, to be able to intervene early sometimes and intervene late sometimes, depending on what is required. The regulation thus adapts itself here, depending on the actual temperature currently prevailing in the detection area. In particular, the respective temperature model ($\Delta FL(T, \Delta T, FL, ZL)$, $\Delta ZL (T, \Delta T, FL,$ ZL))) can thus be adapted accordingly on the basis of a registered value of the detection temperature T. Depending on the currently registered detection temperature, different actuation signals can therefore be generated by the respective stabilization control loop, even with equal relative temperature change $\Delta T$ (in relation to a currently stored reference temperature).

The present method can moreover comprise that the current change $\Delta T$ of the detection temperature is registered in at least two spatially different detection areas, preferably within the imaging optical unit. The advantage results in this way that the probability can be increased of detecting the current change of the detection temperature as early as possible, in order to thus be able to readjust as early as possible. If the change of the detection temperature were only ascertained in one spatial detection area, for example, there would be the risk, for example due to thermal inertia, that a temperature change in the spatial detection area in which the actual cause of this heating is located cannot be registered precisely or early enough and a readjustment of the focusing and/or zoom optical unit then possibly takes place too late. Preferably, a respective current detection temperature T is additionally registered in at least two spatially different detection areas.

Alternatively or additionally, it can be provided that the at least one current temperature change $\Delta T$ is used as an input variable of the at least one stabilization control loop, so that the, in particular respective, stabilization control loop of the stabilization system is triggered, in particular exclusively, by temperature changes. It is thus possible to substantially prevent other non-thermal influencing factors from resulting in an undesired active adjustment of the zoom and/or focusing optical unit. In particular the, in particular respective, stabilization control loop is thus especially not triggered by changes of a current target value for the optical system state.

As already mentioned, the respective temperature threshold value, on the basis of which the respective stabilization control loop of the stabilization system intervenes by control, can depend on the optical system state and/or on at least one (thus in particular on multiple) assigned current detection temperature (measured in a detection area). The stabilization system can thus intervene by control sometimes more and sometimes less strongly/early as needed:

For example, if the zoom factor is set high, a small depth of field (DOF) can result. In this case, the regulation thus already has to intervene when the current position of the focal plane has changed significantly in comparison to the current DOF because of temperature, thus, for example, by 1.0 mm. If the regulation were only to intervene, for example, from a change of the location of the focal plane of 2 mm, the current live image which the surgeon sees would become fuzzy because the temperature regulation has not intervened in a timely manner. Of course, this is absolutely to be avoided.

At long working distance and low zoom level, in contrast, a large field of view and a comparatively large depth of field result. Therefore, it can be reasonable if minor temperature-related drifts of the focal plane are not immediately compensated for by the stabilization system by early adaptation of the focal length.

In contrast, if world coordinates of objects within the camera live image are determined using the described triangulation approach (for instance for the purpose of a navigation or a measurement function) in such a situation, this is particularly susceptible to errors with regard to temperature-related variations of the focal length of the focusing optical unit and the optical zoom level. In such a situation, it can therefore be advantageous to reduce the at least one temperature threshold value, from which the stabilization system initiates an adjustment of the imaging optical unit.

In other words, it can thus be provided that the at least one temperature threshold value is adapted depending on a current operating mode (navigation/measurement/live video imaging with long working distance and low zoom level) of the visualization system.

If the visualization system is designed to be parfocal, for example, the zoom optical unit and the focusing optical unit can be adjusted independently of one another. A temperature drift which acts in such a case on the focusing optical unit then always has the same effect independently of the currently selected zoom level. Thus, if an active adjustment (readjustment) of the focusing optical unit were to become necessary at high zoom level, this temperature stabilization/compensation would also be necessary at low zoom level. However, with respect to a navigation executed using the visualization system, this means that with a zoom level initially set high, the absolute error in the location determination automatically increases (for example from initially 1.5 mm to finally 20 mm) as soon as the zoom level is reduced. At low zoom level, a temperature-related drift of the focusing optical unit therefore has a stronger effect on the determined absolute position than at high zoom level. With respect to the desired temperature stabilization, this means that at high zoom level, a temperature-related drifting away of the focal plane becomes the problem more; at low zoom level, in contrast, it is more the loss of accuracy when navigation is performed (in particular in an automated manner) or a distance in the field of view is measured using the visualization system. The respective adjustment distances of the focusing optical unit necessary for the temperature stabilization are however equal in both cases with parfocal design of the visualization system (thus independently of the current zoom level).

In one design, it can be provided that the current optical system state is only stabilized indirectly by an adaptation of the at least one temperature threshold value. This adaptation can take place, for example, as a result of an externally initiated change of the system state. The stabilization system thus changes itself autonomously, and adapts the regulation to the changed system state. The externally initiated change of the system state can be, for example, a deliberate change of the focusing and/or zoom optical unit here.

Alternatively or additionally, it can be provided that the current optical system state is stabilized by an active adaptation of a current setting of the focusing optical unit and/or the zoom optical unit, in particular as a result of a registered exceeding of the at least one temperature threshold value.

In both cases it can thus occur that the stabilization system intervenes because the at least one temperature threshold value $\Delta T(T)$ is temperature-dependent (and was just adapted by the stabilization system) and a current detection temperature T has changed, so that the previously registered current temperature change now exceeds the adapted temperature threshold value $\Delta T(T)$.

To achieve the object mentioned at the outset, the invention provides a visualization system with one or more of the features disclosed herein. In particular, it is provided according to the invention in the visualization system of the type described at the outset that the imaging optical unit is arranged inside a dust-tight housing and that the at least one detection area is located inside the housing. The advantage can result in this way that the temperature detector is arranged in direct proximity to a source causing the temperature increase, due to which a rapid registration of the temperature increase results. It is particularly preferred here if the at least one temperature detector is arranged in direct proximity to the focusing optical unit.

The dust-tightness of the housing additionally enables cleaning of the housing using disinfectants from the outside without the liquid being able to reach the interior of the visualization system. In particular, it can be provided that the housing is airtight and/or metallic.

The at least one temperature detector can, for example, directly sensorially register the at least one current temperature change (which arises inside the housing for example due to an electrical power loss). Alternatively or additionally, it can moreover be provided that heating which arises inside the housing, for example as a result of an electrical power loss, can be registered at least indirectly or else directly by the temperature detector.

A temperature detector in the meaning of the invention can therefore be understood here to include typical temperature sensors, but also parasitic temperature sensors, as are often already implemented in electronics components, or a (preferably electronic) detector, which estimates a temperature change on the basis of retrieved information (for example a current activity level of an electronic component such as an image sensor or an actuator or an IC), for example by means of a calculation, and thus makes it able to be indirectly registered.

Additionally, it is provided according to the invention that the visualization system comprises a stabilization system having at least one stabilization control loop, using which a current optical system state of the visualization system can be actively stabilized on the basis of the measured and/or indirectly registered at least one current temperature change. It is therefore possible, for example, to prevent the focusing optical unit and/or the zoom optical unit from excessively adjusting due to thermally-related influences (by which the operation of the system would be negatively influenced).

The visualization system, in particular its stabilization system, is preferably configured to carry out a method according to the invention, in particular as described above and/or including one or more of the features described herein.

In the present visualization system, it can moreover advantageously be provided that the at least one temperature detector is arranged inside the housing in direct proximity to optical lenses of the imaging optical unit, for example on a lens frame.

Alternatively or additionally, it can be provided that the at least one temperature detector is arranged at at least one point inside the housing at which thermal expansions of optomechanical components of the imaging optical unit (for example as empirically ascertained and/or as calculated, in particular simulated by means of the "finite element method (FEM)") have a significant influence on a position and/or on an orientation of the focusing optical unit, each in relation to an optical z axis of the imaging optical unit. Since particularly these points are especially critical with respect to the stabilization of the optical system state, the stabilization system can thus intervene by regulation sufficiently early if relevant temperature changes occur at these points.

Alternatively or additionally, the at least one temperature detector can be arranged at at least one point inside the housing at which thermal expansions of optomechanical components of the imaging optical unit have a significant influence on an orientation of the zoom optical unit with respect to an optical z axis of the imaging optical unit.

In a further advantageous embodiment of the invention, it can be provided that the visualization system comprises at least one stepping motor configured to adjust the focusing optical unit and/or the zoom optical unit, in particular mediated via a mechanical spindle. A current focal length of the focusing optical unit and/or the zoom optical unit can therefore be actively readjusted if necessary for example on the basis of a registered temperature change, preferably so that a user of the visualization system does not see a noticeable change in a live video image.

Preferably, at least two stepping motors are designed for adjusting the zoom optical unit and at least one stepping motor is designed for adjusting the focusing optical unit.

For example, it can be provided that classic lenses made of glass are moved with the aid of the respective stepping motor along the or an optical z axis. The stepping motors drive mechanical spindles here, wherein the required mechanical play nonetheless permits tolerances of a few micrometres, so that an accuracy of a few micrometres can be achieved in the adjustment of the respective lens along the z axis.

In particular, each of the stepping motors, in particular mediated via a separate control loop, can be coupled with the at least one stabilization control loop, in particular a respective stabilization control loop, so that the stabilization system can actuate the respective stepping motor for control.

In one advantageous embodiment of the visualization system, it can be provided that the visualization system has at least one control unit for actuating and therefore for adjusting the focusing optical unit and/or the zoom optical unit, in particular with the aid of at least one stepping motor. In this case, the stabilization system is configured to stabilize the current optical system state with the aid of the control unit. Accordingly, a control loop results for the temperature stabilization of the optical system state (but not for temperature regulation).

The optical system state is then preferably stabilized by the stabilization system with the aid of the control unit, even if neither a user nor the visualization system currently seeks a change of the system state or specifies it by means of a new target for the system state.

It can advantageously be provided in one exemplary embodiment of the visualization system that an artificial, preferably electronically implemented, hysteresis is embodied in the stabilization system, in particular as was explained above in detail. It can in particular be ensured by the provision of the artificial/electronic hysteresis, as already mentioned, that upon the adjustment of the respective focusing optical unit/zoom optical unit, a minimum adjustment distance is observed in each case, which is favourable for achieving a high accuracy in the adjustment, in particular if stepping motors are used. The artificial hysteresis can be designed here in particular on the basis of at least one, preferably changeable, temperature threshold value.

The artificial hysteresis in the stabilization system is preferably designed so that the intervention of the stabilization system in the event of temperature changes, which stabilizes the current optical system state, is implemented while avoiding image wobbling, perceptible by a user, of an image recorded by the visualization system. Significantly improved operating properties of the visualization system therefore result for a user, for example a surgeon. The image recorded by the visualization system can be, for example, a live video image, for example in the context of a stereoscopic method.

Alternatively or additionally, a visualization system of the type described at the outset according to the invention is provided in which the visualization system, in particular a stabilization system of the visualization system, is configured to carry out an already mentioned method. The already mentioned advantages of the method can advantageously be implemented in this way.

BRIEF DESCRIPTION OF THE DRAWINGS

The invention will now be described in more detail on the basis of exemplary embodiments, but is not restricted to these exemplary embodiments. Further designs of the invention can be obtained from the following description of a preferred exemplary embodiment in conjunction with the general description, the claims, and the drawings.

In the following description of various preferred embodiments of the invention, elements corresponding in their function receive corresponding reference signs even with differing design or shaping.

In the figures:

Figure 1:
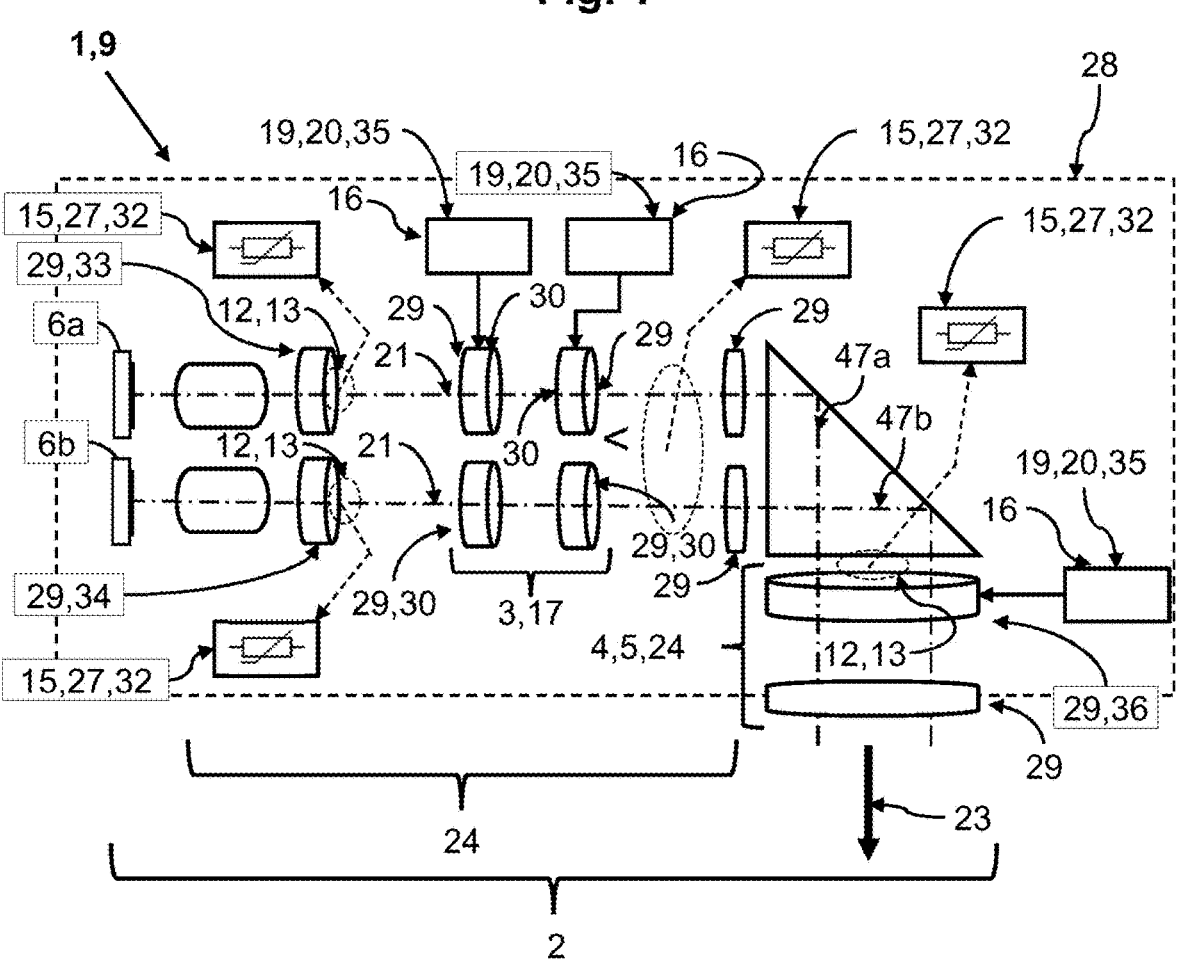
Figure 2:
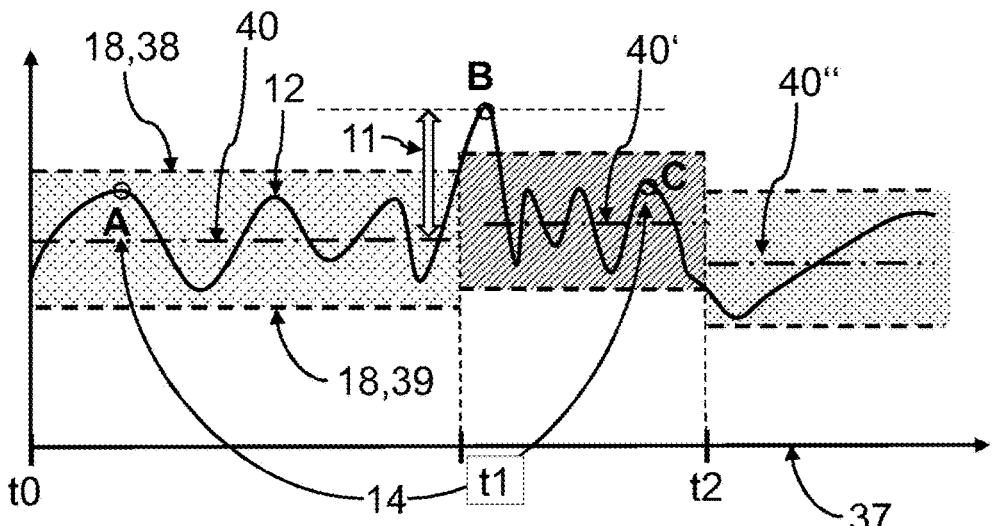
Figure 3:
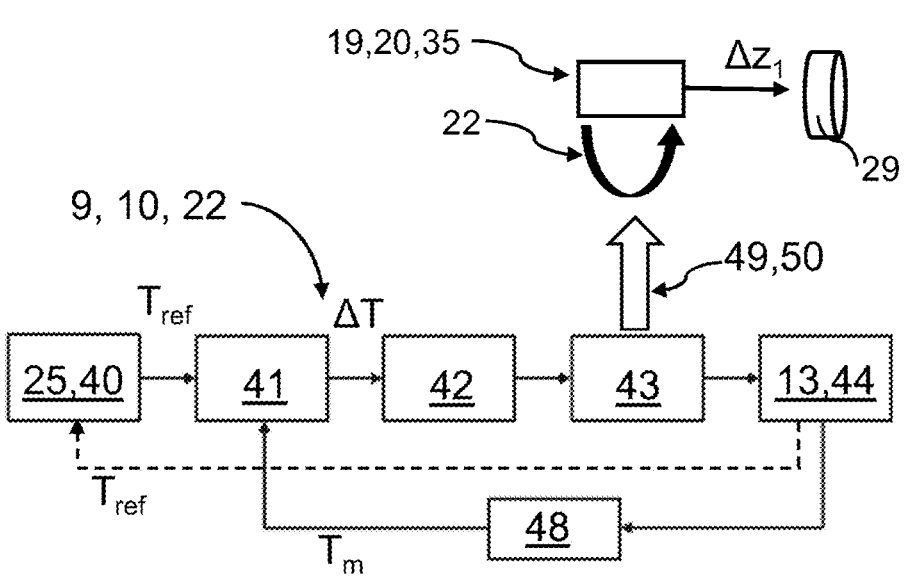
Figure 4:
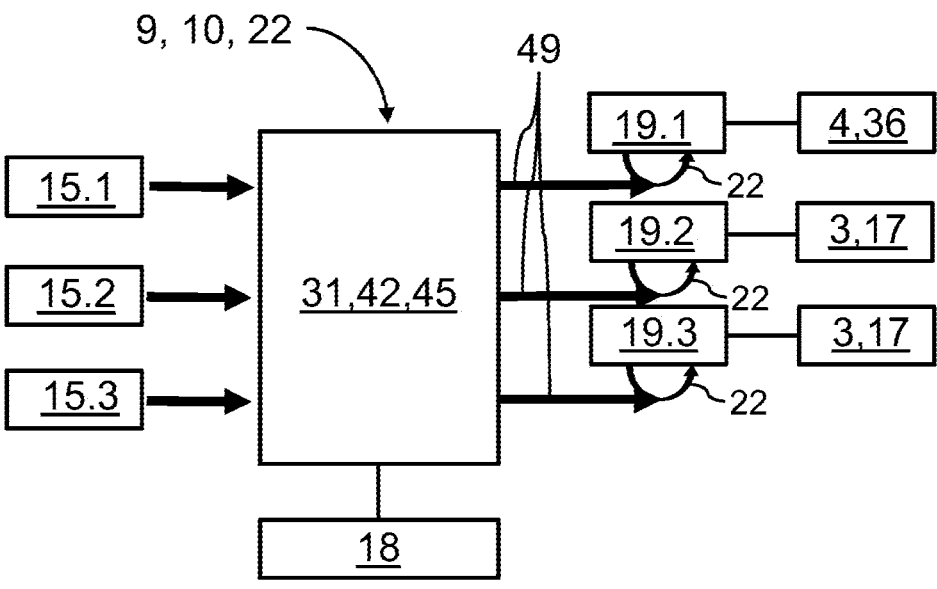
Figure 5:
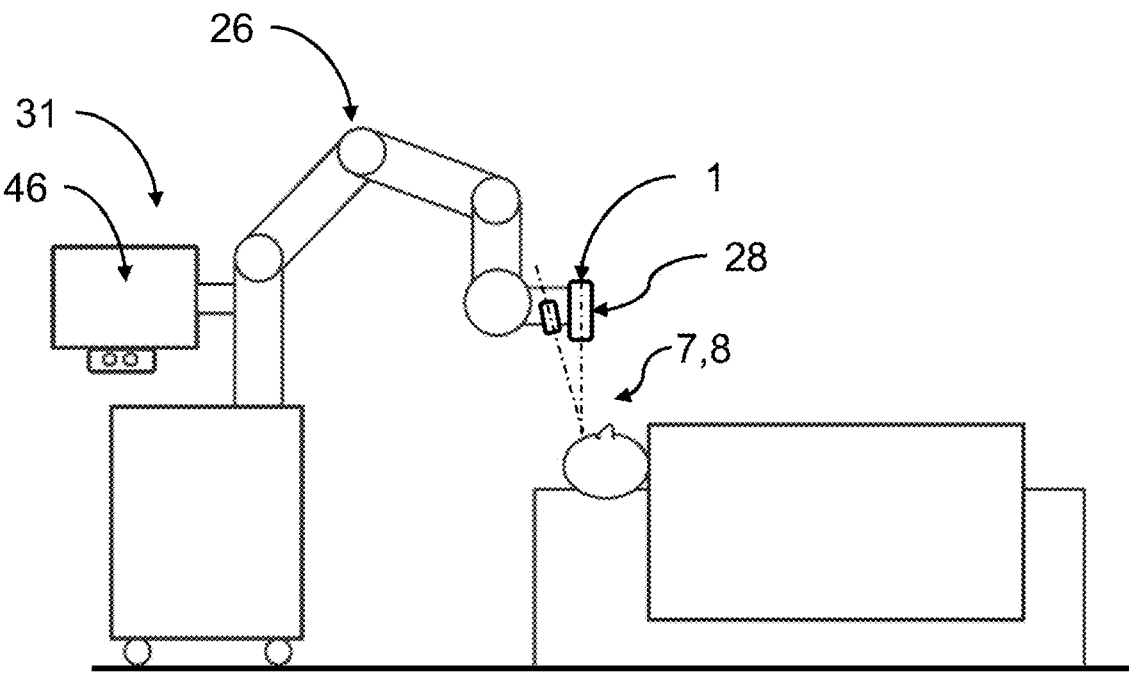

FIG. 1 shows a schematic view of a visualization system according to the invention, FIG. 2 shows the time curve of a detection temperature which is automatically registered inside a housing of the imaging optical unit of the visualization system from FIG. 1, FIG. 3 shows a schematic view of a stabilization control loop of the stabilization system of the visualization system from FIG. 1, FIG. 4 shows a schematic view of the system architecture of the stabilization system of the visualization system from FIG. 1, and finally FIG. 5 shows a typical application situation in which the visualization system according to the invention from FIG. 1 can be used.

DETAILED DESCRIPTION

FIG. 1 illustrates a visualization system 1 according to the invention which, as illustrated in FIG. 5, forms a part of a robotics system 26, using which neurosurgical interventions can be carried out. The entire visualization system 1, which comprises the components listed in claim 13, is mounted here on a movable arm of the robotics system 26 and can therefore be placed at different working distances to the head of the patient and therefore to the operation region 8. The surgeon can observe the images recorded using the image sensor 6 of the visualization system 1 as a live image on the display screen 46 (cf. FIG. 5).

To be able to generate different views of the operation region 8 during the surgical intervention, the visualization system 1 has an adjustable zoom optical unit 3, using which a current optical zoom level 17 can be set, and an adjustable focusing optical unit 4, using which it can be defined on which current focal plane 5 the imaging optical unit 2 is focused-cf. in this regard the structure of the imaging optical unit 2 according to FIG. 1. The focusing optical unit 4 comprises two optical lenses 29 in this case, one of which, which is used as the focus lens 36, can be moved with the aid of the stepping motor 20 shown along the optical z axis, in order to thus adapt the focal length 23.

The zoom optical unit 3 comprises two zoom assemblies, which each comprise multiple optical lenses 29 and which can each be adjusted using an assigned actuator 19 in the form of a respective stepping motor 20.

Furthermore, it can be seen in FIG. 1 that the imaging optical unit 2 is designed as stereoscopic, having two parallel optical channels 47a and 47b, which end in a respective image sensor 6a and 6b. Both optical channels jointly use the focusing optical unit 4 here, while an adjustable zoom optical unit 3 is embodied in each case in the respective channel 47a/47b, which are each adjustable independently of one another with the aid of the respectively assigned two actuators 19. The respective individual images generated by the two image sensors 6a and 6b can be used here to generate a stereoscopic view of the operation region 8. An objective lens 33/34 is arranged between the respective image sensor 6a/6b and the respective zoom optical unit 3 in each of the two optical channels 47a and 47b. The actuators 19 for adjusting the lower zoom optical unit 3 of the second optical channel 47b are not illustrated in FIG. 1 to improve the clarity.

Each of the optical channels 47a and 47b has respective temperature detectors 27 here, which are arranged at different points within a housing 28, which houses the imaging optical unit 2 as a whole in a dust-tight manner. In the example of FIG. 1, these temperature detectors 27 are designed in the form of respective temperature sensors 15, which are capable of directly sensorially measuring a respective detection temperature 12 inside a respective detection area 13. Alternatively thereto, however, it would also be possible for example to only register individual ones of these detection temperatures 12 indirectly, thus non-sensorially. For this purpose, the respective temperature detector 27 can be configured, for example, to estimate a change of a local detection temperature 12 for example on the basis of a registered activity level of an electronic component which generates a thermal power loss, in order to thus indirectly register the temperature change. The temperature detectors 27 arranged at different points inside the imaging optical unit 2 and the detection areas 13 accordingly registered by them are shown in FIG. 1 by dashed ellipses, wherein the temperature detectors 27 are of course not placed in the respective imaging beam path so as not to interfere with the respective optical imaging. All of these detection areas 13 lie inside the housing 28 (shown by dashed lines in FIG. 1), however, which shields the imaging optical unit 2 from the outside world.

As already mentioned at the outset, significant temperature changes can occur for different reasons, which have the result during use of the visualization system 1 (cf. FIG. 5) that the current optical system state, which comprises the current optical zoom level 17 and also the current spatial location of the focal plane defined by means of the focusing optical unit 4 (wherein the respective optical zoom level 17 can even slightly deviate between the two optical channels 47a and 47b), changes in an undesired manner. For example, it can occur that the location of the current focal plane shifts due to a thermal drift inside the imaging optical unit 2 in such a way that the surgeon no longer receives a sharp image of the operation region 8, which can then be very annoying. In order to preventively avoid such situations and in particular to enable the neurosurgeon to be able to concentrate on the actual operation and not themselves have to perform manual adaptations on the visualization system 1, the latter has a stabilization system 9 using which such temperature-related variations of the optical system state can be actively stabilized with the aid of a stabilization control loop 10. In this case, the respective detection temperatures 12 are progressively registered by the stabilization system 9 (directly or at least indirectly).

The system 1 illustrated in FIG. 1 has multiple such stabilization control loops 10 here, wherein FIG. 3 illustrates one of these control loops 10 as an example: proceeding from a current temperature 25, which is progressively registered as the detection temperature 12 with the aid of one of the temperature detectors 27 within the detection area 13 monitored by the temperature detector 27, a comparator 41 compares this current measured value to a current reference temperature 40 (=saved/currently stored value, which is used as a reference point for the control loop). Due to this comparison, the stabilization system 9 therefore registers a current temperature change 11 in relation to the current reference temperature 40 and calculates therefrom in a calculation step 42 a new position of the focusing optical unit 4 and of the zoom optical unit 3 for the optical channel 47a/47b, in which the temperature detector 27 is arranged.

If, for example, a significant temperature change 11 in the area of the jointly used focusing optical unit 4 in relation to the current reference temperature 40 is registered, the stabilization system 9 can not only intervene by regulation on the focusing optical unit 4 and actively adjust this accordingly, but also can additionally act by control on both zoom optical units 3 of the two optical channels 47a, 47b (only one such path for a lens 29 is illustrated in FIG. 3). In the example shown in FIG. 3, the stabilization system 9, more precisely the illustrated stabilization control loop 10, therefore initiates a respective change 43 of the position or the setting of the focusing optical unit 4 and/or the zoom optical unit 3.

The precise size and direction of the respective active adjustment to be performed of the focusing optical unit 4 and/or the zoom optical unit 3 is calculated here by the stabilization system 9 on the basis of a respective temperature model. The respective temperature model (for example $\Delta FL(T, \Delta T, FL, ZL)$) for determining a required active adjustment describes here the temperature behaviour of the respective optical unit 3/4, and does so independently of the currently assumed reference temperature 40 (=T), the registered temperature change 11 (=$\Delta T$), and the currently set zoom level (ZL) and focal length (FL) of the focusing optical unit 4 (from which the current location of the focal plane results).

In step 43, the focusing optical unit 4 and/or the zoom optical unit 3 is therefore actively adjusted by the stabilization control loop 10. However, steps 42 and 43 only take place if a current temperature threshold value 18 has also actually been exceeded with respect to the previously registered current temperature change 11.

Since the detection temperature 12 is progressively registered, an update of the reference temperature 40 (dashed arrow) also takes place in step 44, which can be carried out, for example, using a measurement 48 or alternatively by means of an updated estimation of the detection temperature 12. In particular a temperature registered at the time of the active adjustment of the imaging optical unit 2 can be used as the reference: if, for example, a temperature of 25° C. was registered, which is already above a threshold value 18 of 24° C., and thereupon an active adjustment of the imaging optical unit 2 was carried out, the new reference value can be adapted to 25° C. In other words, the reference temperature 40 for a specific detection temperature 12 of a specific detection area 13 is preferably always updated as soon as the associated stabilization control loop 10/the stabilization system 9 intervenes by control in the imaging optical unit 2.

The reference temperature 40 can be defined, for example, on the basis of a calculation rule, proceeding from the temperature registered at the time of the compensation. However, it can also be defined, for example, that an adjustment takes place if a defined first temperature threshold value (for example T=23° C.) is exceeded and the next adjustment only takes place again upon exceeding a second likewise defined temperature threshold value (for example T=26° C.).

A temperature stabilization in the meaning of the invention can thus in principle take place in two ways:

A) The at least one temperature threshold value remains unchanged. If, for example, an adjustment is carried out in such a case due to exceeding a first temperature threshold value at 23.0° C. and then 25.8° C. is measured, an adjustment will only again be carried out in the case of further increasing temperature and reaching a second temperature threshold value of 26° C. This approach A) thus provides unchanging threshold values, so that the stabilization system always intervenes at the same temperatures.

B) However, the reference temperature can also be shifted, for example by means of a temperature delta (cf. FIG. 2), i.e. an adjustment of the imaging optical unit with respect to a currently measured temperature of, for example, 25.8° C. is then carried out and the temperature threshold value is shifted upwards by a fixed value, for example, 1.5° C., thus for example to 27.3° C. as the upper threshold and 24.3° C. as the lower threshold. This approach B) thus provides actively carrying along the threshold values as soon as the stabilization system intervenes by adjustment, so that the temperatures from which the stabilization system intervenes can change progressively. The amount by which the respective temperature threshold value is shifted can be derived here from at least one temperature which the stabilization system 9 currently registers.

Moreover, it can be seen in FIG. 3 that the stabilization control loop generates a respective actuation signal 49, which is used for adjusting the zoom optical unit 3 and/or the focusing optical unit 4 (only one of these signals 49 is illustrated as an example in FIG. 3). In the example shown, the stabilization system 9, more precisely the stabilization control loop 10 shown, intervenes in a separate control loop 22 here, using which one of the lens actuators 19 is regulated, in order to thus move the lens 29 by a specific distance $\Delta z1$.

The stabilization control loop 10 can in this way, in step 43, transfer, for example, control parameters 50 for adapting respective lens positions to the suitable control loop 22 so that then the actuator 19 causes a corresponding adjustment of the lens 29. Under certain circumstances, this takes place even if neither the visualization system 1 nor the user has specified a new optical system state as a target specification. Therefore, even if neither the robotics system 26 nor the user wishes to set a different focal plane, the stabilization system 9 can nonetheless actively adjust the focusing optical unit 4 autonomously, in reaction to a registered current temperature change 11 and in particular in consideration of the current optical system state, in order to thus preventively counteract a temperature-related drift of the optical system state. The imaging is thus actively stabilized, so that the surgeon can concentrate on the surgical intervention.

One challenge in this regulation approach is for the surgeon not to feel annoyed in that the stabilization system 9 adjusts the zoom optical unit 3 and/or the focusing optical unit 4 continuously and thus in an annoying manner. For this reason, the stabilization control loop 10 is equipped with an artificial hysteresis, so that the visualization system 1 can be in different optical system states at the same temperature, depending on how the currently registered detection temperature 12 was reached, thus, for example, due to a temperature rise or else due to a temperature drop.

This approach can be comprehended well, for example, on the basis of FIG. 2: the time curve of a detection temperature 12 registered with the aid of a temperature sensor 15 of the visualization system 1 can be seen therein. The stabilization system 9 registers the current temperature change 11 here at regular time intervals as the difference between the currently registered detection temperature 12 and a currently stored reference temperature 40. As long as this progressively registered temperature change 11 ∆T remains within the limits defined by the two temperature threshold values 38, 39, the stabilization system 9 does not intervene.

However, after the upper temperature threshold value 38 was exceeded at time t1, the stabilization system 9 thus intervenes to stabilize, unchanged, the optical system state which was changed previously due to the occurring temperature change 11 in such a way that it is stabilized again. The adjustment of the focusing optical unit 4 and/or the zoom optical unit 3 caused by the intervention of the stabilization system 9 is illustrated in FIG. 2 on the basis of the changing shading. Exceeding of the temperature threshold value 18 is understood by the invention here thus as exceeding the respective temperature limit 38/39: this can take place in the positive or in the negative direction, as can be comprehended well on the basis of FIG. 2. Depending on the design, the temperature threshold values 38, 39 can also be at different distances from the reference temperature 40 (=asymmetric temperature interval).

It can be seen here that the stabilization control loop 10 has a hysteresis 14 when the two times A and C are compared to one another: although the same detection temperature 12 exists/is registered at both times, the two optical units 3 and 4 are in different settings, namely because point A was reached by a slight temperature increase still within the two limits 38 and 39, while point C, starting from time B, was reached after a drop of the temperature and after exceeding the upper temperature threshold value 38.

At time t2, in contrast, the currently registered detection temperature 12 falls below the lower temperature threshold value 39 again, whereupon the stabilization control loop 10 again intervenes by regulation in order to again stabilize the optical system state. The changed setting of the two optical units 3 and 4 resulting therefrom is again illustrated by a differing shading. Furthermore, it can be seen that whenever the stabilization control loop 10 intervenes by control/adjusting of the optical units 3 and/or 4, the stored reference temperature 40 and also the location of the upper and lower temperature threshold value 38, 39 is also adapted accordingly. Therefore, for example, the stabilization control loop 10 already intervenes, for example, at time t2 at a detection temperature 12, at which it would not yet have intervened in the time interval t0 to t1. In other words, the temperature threshold values 38, 39 are thus each selected here depending on the currently stored reference temperature 40. The system could also, depending on the level of the currently stored reference temperature 40, adapt the temperature interval defined by the two temperature threshold values 38, 39, in which the stabilization control loop 10 does not yet intervene, in its size (and therefore define early or rather late intervention, depending on the requirements of the application and/or the imaging optical unit 2 used).

FIG. 4 illustrates a possible implementation of a stabilization system 9 according to the invention: this comprises a control unit 31, implemented by means of a microcontroller 45, which is configured to calculate new positions of the focusing optical unit 4 or the zoom optical unit 3 on the basis of multiple respective detection temperatures 12 registered by means of temperature sensors 15.1, 15.2 and 15.3 (calculation step 42). In this case, the microcontroller 45 also takes into consideration a current temperature threshold value 18. This is also adapted in each case, like a respective current reference temperature 40, by the control unit 31 depending on the current optical system state and depending on at least one of the three different detection temperatures 12.

The microcontroller 45 implements multiple stabilization control loops 10 here, which can be constructed, for example, analogously to that of FIG. 3. The control unit 31/the microcontroller 45 intervenes in each case by control with the aid of a respective actuation signal 49 in a respective separate control loop 22, using which a respective assigned actuator 19 is operated. In this way, the control unit 31, as illustrated in FIG. 1, can actively adjust the two assemblies of the zoom optical unit 3 and the common focusing optical unit 4 as needed and thus ultimately stabilize both the zoom level 17 and the focal length 23 and therefore the location of the focal plane.

In summary, for improved operation of a visualization system 1, which comprises an imaging optical unit 2 having an adjustable zoom optical unit 3 and a likewise adjustable focusing optical unit 4, it is provided that with the aid of at least one temperature detector 27, at least one detection temperature 12 inside the imaging optical unit 2 is registered, either directly sensorially or else indirectly (for example by means of an estimation) and that with the aid of a stabilization system 9, which comprises one or more stabilization control loops 10, the focusing optical unit 4 and/or the zoom optical unit 3 is actively adjusted as soon as a temperature threshold value 18 is exceeded with respect to a currently registered temperature change 11 of this detection temperature 12 (cf. FIG. 1).

LIST OF REFERENCE SIGNS

1 visualization system
2 imaging optical unit
3 zoom optical unit
4 focusing optical unit
5 focal plane
6 image sensor
7 observed object
8 operation region
9 stabilization system
10 stabilization control loop
11 temperature change
12 detection temperature
13 detection area
14 hysteresis
15 temperature sensor
16 electronic component
17 zoom level
18 temperature threshold value
19 actuator
20 stepping motor
21 Z axis
22 control loop
23 focal length
24 adjustment distance
25 currently registered temperature
26 robotics system
27 temperature detector
28 housing

29 lens
30 lens frame
31 control unit
32 thermistor
33 objective lens 1
34 objective lens 2
35 electric motor
36 focus lens
37 time axis
38 upper temperature threshold value
39 lower temperature threshold value
40 reference temperature
41 comparator
42 calculation of a new position of the focusing optical unit/zoom optical unit
43 change of the position
44 update of the registered detection temperature (as the current measured value/as a reference temperature for the control loop)
45 microcontroller
46 display screen
47 optical channel
48 measurement of 12
49 actuation signal
50 control parameter
15.1 temperature sensor 1
15.2 temperature sensor 2
15.3 temperature sensor 3
19.1 actuator 1
19.2 actuator 2
19.3 actuator 3

The invention claimed is:

1. A method for temperature stabilizing a current optical system state of a visualization system, which comprises an imaging optical unit having an adjustable zoom optical unit for defining a current optical zoom level, an adjustable focusing optical unit for defining a current spatial location of a focal plane, and at least one image sensor, the method comprising:

recording at least one image of an object observed using the visualization system using the at least one image sensor, and stabilizing a current optical system state, which comprises the current optical zoom level and the current spatial location of the focal plane, in relation to temperature-related variations within the imaging optical unit, providing a stabilization system, which comprises at least one stabilization control loop, and progressively registering at least one current temperature change of a detection temperature within at least one detection area within the visualization system, directly or indirectly, and actively adjusting at least one of the focusing optical unit or the zoom optical unit by the at least one stabilization control loop as soon as at least one temperature threshold value for the at least one current temperature change is exceeded.

2. The method according to claim 1, wherein to avoid image wobbling of the at least one recorded image, the at least one stabilization control loop is designed having an artificial hysteresis, such that the at least one stabilization control loop, depending on the current optical system state and depending on a direction of the registered current temperature change, automatically initiates different adjustments of at least one of the focusing optical unit or the zoom optical unit.

3. The method according to claim 2, wherein the automatically initiated different adjustments are carried out independently of whether currently a new target value is specified for an adjustment of the at least one of the focusing optical unit or the zoom optical unit from outside the at least one stabilization control loop or not.

4. The method according to claim 1, further comprising at least one of a) registering the detection temperature at least one of directly sensorially with the aid of a temperature sensor or indirectly, by calculation based on a current electrical power loss of an electronic component of the visualization system, b) progressively registering the respective detection temperature as a respective current temperature, c) determining the temperature change in relation to a stored reference temperature, or d) at least one of adapting or updating the reference temperature as soon as the stabilization system intervenes by regulation/control.

5. The method according to claim 1, wherein the respective adjustment of the at least one of the focusing optical unit and/or the zoom optical unit, depending on the current optical system state, takes place at different times in relation to the registered at least one current temperature change, and the at least one temperature threshold value is adapted for this purpose depending on the current optical system state.

6. The method according to claim 1, wherein the at least one stabilization control loop operates even if no new optical system state is specified by the visualization system itself or by a user as a target specification, so that an optical system state set once is progressively stabilized by the stabilization system in relation to temperature variations.

7. The method according to claim 1, wherein, upon exceeding at least one of the at least one temperature threshold value or at least one position threshold value, the at least one stabilization control loop actuating at least one actuator of at least one of the focusing optical unit or the zoom optical unit to adjust at least one of the focusing optical unit or the zoom optical unit along an optical z axis of the imaging optical unit.

8. The method of claim 7, wherein the at least one stabilization control loop actuates the respective actuator mediated via a separate respective control loop, with the aid of which the actuator is adjustable in a regulated manner.

9. The method according to claim 1, further comprising the stabilization system adjusting, independently of a respective target value, previously set by the user or by the visualization system, the at least one of the focusing optical unit or the zoom optical unit by control as soon as the at least one current temperature change of the detection temperature exceeds an assigned temperature threshold value still permitted for the current optical system state.

10. The method according to claim 1, wherein the stabilization system adjusts the at least one of the focusing optical unit or the zoom optical unit for control based on a respective temperature model in order to stabilize the current optical system state in relation to the registered at least one current temperature change, and the respective temperature model models a required temperature-dependent adjustment of the focusing optical unit or the zoom optical unit.

11. The method according to claim 10, further comprising the stabilization system calculating a suitable compensating adjustment of the at least one of the zoom optical unit or the focusing optical unit based on the registered at least one current temperature change and generating therefrom a respective actuation signal for adjusting the at least one of the zoom optical unit or the focusing optical unit, in order to thus stabilize the current optical system state depending on the temperature.

12. The method according to claim 10, wherein the stabilization system takes into consideration a registered value of the current detection temperature T and adapts at least one of a) the at least one temperature threshold value $\Delta T_{max}(T)$, from which the stabilization system intervenes by control, or b) the respective temperature model based on the registered value of the detection temperature T.

13. The method according to claim 1, wherein at least one of a) a current change $\Delta T$ of the detection temperature is registered in at least two spatially different detection areas, or b) the at least one current temperature change is used as an input variable of the at least one stabilization control loop, so that the stabilization control loop of the stabilization system is triggered by temperature changes, but not by changes of a current target value for the optical system state.

14. The method according to claim 1, wherein the current optical system state is stabilized at least one of a) indirectly by an adaptation of the at least one temperature threshold value as a result of an externally initiated change of the system state, or b) by an active adaptation of a current setting of the at least one of the focusing optical unit or the zoom optical unit, and wherein the stabilization system intervenes, because the at least one temperature threshold value is temperature-dependent and a currently registered temperature T has changed, so that the previously registered current temperature change now exceeds an adapted temperature threshold value $\Delta T(T)$.

15. A visualization system, comprising:

an imaging optical unit, which includes:

an adjustable zoom optical unit for defining a current optical zoom level, an adjustable focusing optical unit for defining a current spatial location of a focal plane, at least one image sensor for recording at least one image of an object observed using the visualization system, and at least one temperature detector, which is configured for at least one of direct sensorial measurement or for the indirect non-sensorial registration of at least one current temperature change of a detection temperature within at least one detection area;

a dust-tight housing in which the imaging optical unit is arranged, the dust-tight housing having the at least one detection area located therein;

a stabilization system having at least one stabilization control loop, via which a current optical system state of the visualization system is adapted to be actively stabilized based on the measured and/or indirectly registered at least one current temperature change.

16. The visualization system according to claim 15, wherein the at least one temperature detector is arranged at least one of inside the housing in direct proximity to optical lenses of the imaging optical unit, or at at least one point inside the housing, at which thermal expansions of optomechanical components of the imaging optical unit have a significant influence on at least one of a position or on an orientation of the at least one of the focusing optical unit or the zoom optical unit, each in relation to an optical z axis of the imaging optical unit.

17. The visualization system according to claim 15, further comprising at least one stepping motor, which is configured to adjust the at least one of the focusing optical unit or the zoom optical unit, and each said stepping motor is coupled with the at least one stabilization control loop so that the stabilization system is adapted to actuate by control the respective at least one stepping motor.

18. The visualization system according to claim 17, further comprising at least one control unit for actuating and therefore adjusting the at least one of the focusing optical unit or the zoom optical unit using the at least one stepping motor, and wherein the stabilization system is configured to stabilize the current optical system state with the aid of the control unit.

19. The visualization system according to claim 15, wherein an artificial hysteresis is designed in the stabilization system, based on at least one temperature threshold value, so that the intervention of the stabilization system stabilizing the current optical system state in the event of temperature changes is implemented while avoiding image wobbling perceptible for a user of an image recorded by the visualization system.

20. The visualization system according to claim 15, wherein the visualization system is configured to carry out the steps of:

recording at least one image of an object observed using the visualization system using the at least one image sensor, and stabilizing a current optical system state, which comprises a current optical zoom level and a current spatial location of a focal plane, in relation to temperature-related variations within the imaging optical unit, the stabilization system progressively registering at least one current temperature change of a detection temperature within at least one detection area within the visualization system, directly or indirectly, and actively adjusting at least one of the focusing optical unit or the zoom optical unit by the at least one stabilization control loop as soon as at least one temperature threshold value for the at least one current temperature change is exceeded.

* * * * *